US008325053B2

(12) United States Patent
Flynt et al.

(10) Patent No.: US 8,325,053 B2
(45) Date of Patent: Dec. 4, 2012

(54) PERSONAL FALL PROTECTION MONITORING SYSTEM

(75) Inventors: William N. Flynt, Hillsboro, NH (US); Shawn A. Remington, Oak Ridge, TN (US); Jacob M. Martin, Oak Ridge, TN (US); Timothy Vile, Rutland, VT (US)

(73) Assignee: JCJ Inc., Knoxville, TN (US)

( * ) Notice: Subject to any disclaimer, the term of this patent is extended or adjusted under 35 U.S.C. 154(b) by 329 days.

(21) Appl. No.: 12/720,912

(22) Filed: Mar. 10, 2010

(65) Prior Publication Data
US 2010/0231402 A1 Sep. 16, 2010

Related U.S. Application Data

(60) Provisional application No. 61/158,918, filed on Mar. 10, 2009.

(51) Int. Cl.
*G08B 21/00* (2006.01)

(52) U.S. Cl. ........ 340/679; 340/680; 340/681; 340/682; 340/573.1; 182/3; 182/4; 182/5; 182/6; 182/7; 182/231; 182/232; 182/233; 182/234; 182/235

(58) Field of Classification Search .......... 340/679–685, 340/573.1; 182/3–9, 231–234
See application file for complete search history.

(56) References Cited

U.S. PATENT DOCUMENTS 6,330,931 B1 * 12/2001 Baillargeon et al. ............ 182/18
7,106,205 B2 9/2006 Graef
7,490,610 B2 2/2009 Franklin
7,636,990 B1 12/2009 Choate
2009/0080909 A1 * 3/2009 Usui et al. ........................ 399/13
2009/0173578 A1 * 7/2009 Renton et al. ................. 182/235
2009/0249712 A1 * 10/2009 Brickell et al. .............. 52/173.1

FOREIGN PATENT DOCUMENTS

JP 2007 044166 2/2007
WO WO 2008/120022 A1 10/2008

* cited by examiner

*Primary Examiner* — George Bugg
*Assistant Examiner* — Ojiako Nwugo
(74) *Attorney, Agent, or Firm* — Knox Patents; Thomas A. Kulaga (57) ABSTRACT

Apparatus for monitoring compliance with the 100% tied off rule for climbers using personal fall protection equipment. The personal fall protection monitoring system includes a remote monitoring module that monitors multiple harness systems. Each harness system includes sensors that detect the engagement of the lanyard with anchorage points and the harness. The system also includes a harness module that monitors the sensors and indicates an alarm condition to the climber and to the remote monitoring module. The harness module includes a transmitter that communicates with the remote monitoring module. The remote monitoring module communicates with multiple harness systems to indicate and log the status of each harness system.

18 Claims, 7 Drawing Sheets

PERSONAL FALL PROTECTION MONITORING SYSTEM

CROSS-REFERENCE TO RELATED APPLICATIONS

This application claims the benefit of U.S. Provisional Application No. 61/158,918, filed Mar. 10, 2009.

STATEMENT REGARDING FEDERALLY SPONSORED RESEARCH OR DEVELOPMENT

Not Applicable

BACKGROUND OF THE INVENTION

1. Field of Invention

This invention pertains to personal fall protection monitoring system. More particularly, this invention pertains to a system that monitors compliance to the 100% tied off rule for a climber.

2. Description of the Related Art

A climber of an elevated structure requires safety equipment. Climbers include steel workers, riggers, and communication and power transmission tower climbers, among others. Elevated structures include steel structures, oil rigs, communication towers, and electrical power transmission towers, and the like. To ensure safety when aloft, tower climbers are required to be attached to an anchorage at all times. The safety equipment used by climbers includes personal fall protection equipment and positioning equipment.

Personal fall protection equipment includes fall prevention equipment, such as a tether system. The tether system includes a harness, an anchorage point, and a connecting device. A harness is a device worn by the climber. Examples of harnesses include a full body harness, a waist belt, or other device that is worn or attached to the climber. The object being climbed provides anchorage. An anchorage point is a secure point of attachment on the object being climbed for lifelines, lanyards, or deceleration devices. The anchorage point must have sufficient strength to support the person climbing the object, including the forces generated during a fall.

A connecting device is a lanyard or tether that connects the harness to the anchorage point. To ensure 100% fall protection, a Y-lanyard is often used. The Y-lanyard has a single lanyard hook that attaches to the harness and the opposite end of the lanyard is divided into two straps, each with a lanyard hook for attaching to an anchorage point. As the climber moves, the second lanyard hook is attached before the first is removed from the anchorage point.

Positioning equipment includes a body belt or body harness rigged to allow a climber to be supported on an elevated vertical surface, such as a wall, and work with both hands free while leaning. The equipment includes an anchorage point, a belt or harness, and a connecting device. Positioning equipment should be used only for the assistance for which they are designed, they are not relied upon to provide fall arrest.

BRIEF SUMMARY OF THE INVENTION

According to one embodiment of the present invention, a harness monitoring system is provided that monitors the engagement of the lanyard with an anchorage point and alarms the condition where the climber is not tied off 100% of the time aloft. The alarm condition is indicated to the climber and to a remote module. The monitoring system does not rely upon the climber following procedures, instead, the system monitors for the situation where the climber does not follow procedures by not using the safety equipment properly. In one such embodiment, the remote module logs the compliance of the climber and communicates that compliance information to a third party. In this way an insurance company or off-site manager has access to the compliance information.

In one embodiment, a personal fall protection monitoring system includes a harness monitoring system for each climber and a remote monitoring module that is used by a person on the ground, such as a supervisor. The harness monitoring system includes a harness module and lanyard sensors. The lanyard sensors sense if the lanyard hooks are attached and the harness module monitors the lanyard sensors and provides an alarm if there is not at least one connection between the climber's harness and the tower. The alarm is provided locally to the climber and remotely to the remote monitoring module though a transmitter in the harness module.

The remote monitoring module includes a receiver that communicates with each harness monitoring system. The remote monitoring module also includes indication of the status of each harness monitoring system and a data logger that stores status information for later communication to another device.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Apparatus for a personal fall protection monitoring system 100 is disclosed. The system 100 is suitable for use by climbers, such as steel workers, riggers, and tower climbers, that need to be tied off 100% of the time.

Figure 1:
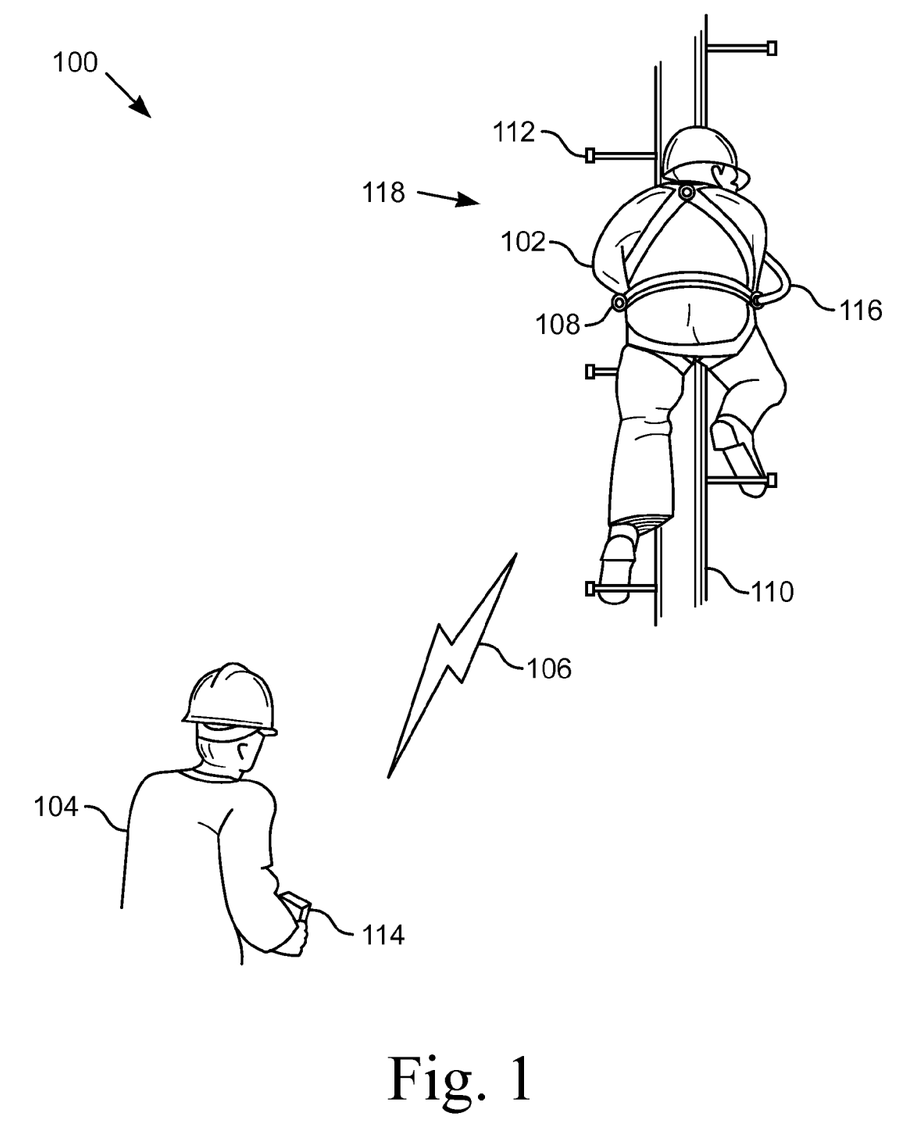
FIG. 1 is a symbolic view of one embodiment of a personal fall protection monitoring system.

FIG. 1 illustrates a symbolic view of one embodiment of a personal fall protection monitoring system 100. The monitoring system 100 includes a remote monitoring module 114 and a harness system 118. A climber 102 is a person who ascends, descends, moves point-to-point, or otherwise is on a tower 110 or other object that requires the climber 102 to be elevated above the ground. The climber 102 wears a harness 108, which is secured to anchorages on the tower 110 by a lanyard, or connecting device, 116. In the illustrated embodiment, the climber 102 uses step bolts 112, which are suitable as anchorage points if the step bolts 112 meet certain requirements.

The climber 102, depending upon the work to be performed and the type of tower 110 being climbed, uses various lanyards 116 and fall arrestors. Lanyards 116 have various configurations, such as a straight, or single leg, lanyard 116 or a Y-lanyard, or two-legged lanyard, 116-Y, and often include a shock absorbing device 314, particularly when the lanyard 116 is also used as a fall arrestor. Lanyards 116 used for body positioning typically do not include, and do not require, a shock absorbing device.

The remote monitoring module 114 is a device carried by a person 104, such as a foreman, supervisor, manager, or other person who desires to monitor one or more climbers 102 to ensure compliance with the 100% tied off rule. In one embodiment, the remote monitoring module 114 is a portable device suitable for handholding or attaching to a garment or harness worn by the monitoring person 104. The 100% tied off rule requires that, above a certain elevation, the climber must always, 100% of the time, have a secure, physical connection to an anchorage point. For a climber of a tower 110, such as a communications tower, this means that the climber 102 must always have a lanyard 116 hooked to the harness 108 and the other end of the lanyard 116 must be hooked to an anchorage point or the climber 102 must be secured to the tower 110 with a fall arrest device. When moving around when aloft, the climber 102 must use either a Y-lanyard 116 in which at least one of the outboard lanyard hooks 310 is connected to an anchorage or two straight lanyards 116 in which at least one lanyard 116 is connected.

The remote monitoring module 114 receives a wireless signal 106 from the harness system 118. The wireless signal 106 includes information identifying the harness system 118 and the status of the harness system 118. The identification of the harness system 118, includes, in various embodiments, a unique identifier and/or the name of the climber 102 wearing the harness system 118. Because each harness system 118 is uniquely identified, the remote monitoring module 114 monitors multiple harness systems 118, such was when several climbers 102 are on the tower 110. The wireless signal 106 provides the status of the harness system 118, and the status includes information on whether the harness 108 is connected to at least one anchorage point. If there is no connection between the harness 108 and any anchorage, the status information includes an alarm, which is indicated on the remote monitoring module 114.

The remote monitoring module 114 also includes a data logging feature in which the status of each harness system 118 in use is logged for a period, creating a data log. The data log provides information that is suitable for use by others to verify compliance with the 100% tied off rule. For example, management of the company responsible for some aspect of the work may wish to verify compliance, and/or an insurance company may wish to verify compliance by the climbers 102.

Figure 2:
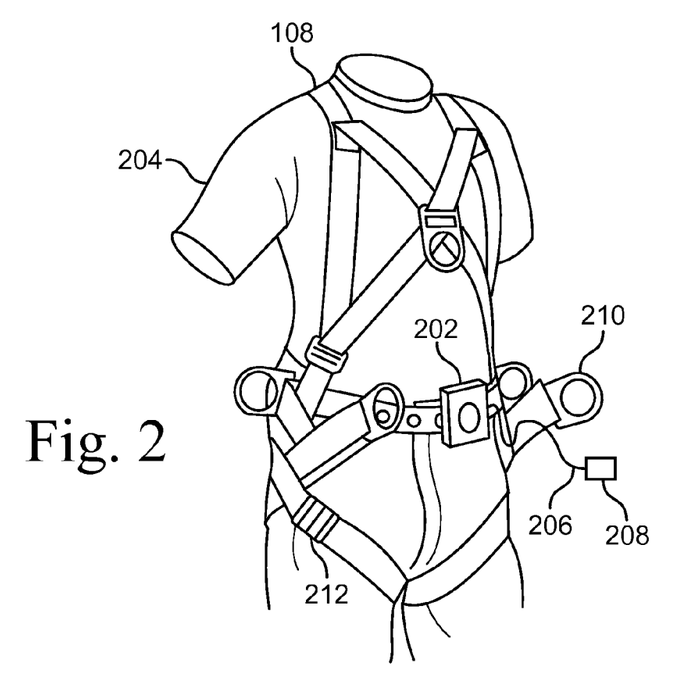
FIG. 2 is a block diagram of one embodiment of a remote monitoring module.

FIG. 2 illustrates a perspective view of one embodiment of a harness 108 with a harness module 202. The illustrated harness 108 is a tower climbing harness shown on clothing 204 such as worn by a climber 102. The harness 108 includes multiple D-rings 210 positioned to provide positioning support attachment anchors and fall arresting anchors and for attaching accessories. Harnesses 108 have various configurations that are adapted to the type of work to be performed by the climber 102. For example, climbers 102 who work from platforms and do not have a need for positioning support often wear harnesses 108 without a belt. Other climbers 102 wear harnesses 108 that include shoulder retrieval D-rings and/or a seat cushion for comfort.

The illustrated embodiment shows a harness module 202 secured to the belt of the harness 108. Extending from the harness module 202 is a cable 206 that terminates in a harness connector 208. In one embodiment, the cable 206 is stitched or otherwise secured to the webbing of the harness 108. By being so secured, the cable 206 is less likely to be damaged by snagging or from abrasion when the harness 108 is worn by the climber 102. In one embodiment, a harness connector 208 is positioned adjacent each D-ring 210 that is available for use to satisfy the 100% tied off rule. In one embodiment, the cable 206 plugs into a connector on the harness module 202, thereby allowing the module 202 to be removed from the harness 108. In another embodiments, a wireless connection is used instead of the wired connection 206, 208.

Figure 3:
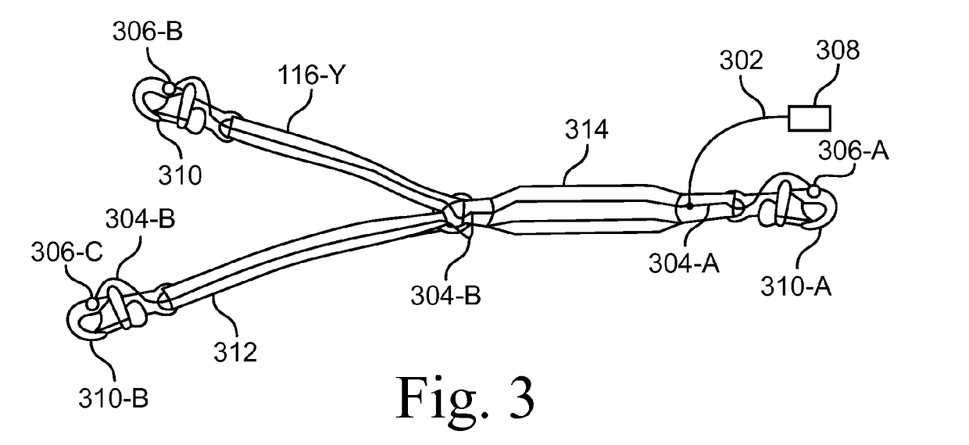
FIG. 3 is a perspective view of one embodiment of a harness with a harness module.

FIG. 3 illustrates a plan view of one embodiment of a Y-lanyard 116-Y. The lanyard 116-Y has three lanyard hooks 310 that are connected to each other with flexible members 312. The illustrated lanyard 116-Y includes a shock absorbing device 314 adjacent the harness lanyard hook 310. The illustrated lanyard hooks 310 are locking snap hooks, but in other embodiments, the lanyard hooks 310 are suited to be attached to the particular anchorages 112 available on the tower 110. For example, the outboard, or tower, lanyard hooks 310-B are pelican hooks or rebar hooks. Reference number 310 is used herein to refer to the lanyard hook 310 in general. The various illustrated embodiments add a suffix to the 310 reference number to identify the specific embodiment of lanyard hook 310.

Incorporated in the lanyard 116-Y is a lanyard connector 308 that mates to the harness connector 208 on the harness 108. The lanyard connector 308 allows for quick and convenient connection of different types of lanyards 116 to the harness connector 208 thereby ensuring that the correct lanyard 116 for the climbing environment is used. Extending from the lanyard connector 308 to the lanyard member 312 is a pigtail 302. In one embodiment, the lanyard cable 312 is a reinforced, flexible cable that is secured to the lanyard member 312 and is able to withstand tugs and pulling forces.

The pigtail 302 connects to a lanyard cable 304-A that is stitched or otherwise secured to the lanyard members 312. Where the lanyard cable 304-B crosses or extends over a joint, such as where the lanyard member 312 attaches to the lanyard hook 310, the lanyard cable 304-B has a loop of slack cable that allows the joint to flex without stressing the lanyard cable 304-B.

Each end of the lanyard cable 304 terminates at a hook sensor 306 that detects if the lanyard hook 310 has engaged an anchorage point 112 or a harness D-ring 210. The hook sensor 306 is a device that detects a condition indicating the presence of the anchorage 112. In one embodiment, the sensor 306 is a switch that is actuated physically when an object is encompassed by the lanyard hook 310. In another embodiment, the sensor 306 is part of a ground detection circuit that detects when the lanyard hook 310 is in contact with a grounded, metal object, such as a metal tower 110. In other embodiments, the sensor 306 is a device that is responsive to eddy currents, ferrous metals, or another characteristic of anchorage points 112 used on towers 110. In yet another embodiment, the sensor 306 is a proximity detector sensitive to objects within the throat of the lanyard hook 310.

In one embodiment, each hook sensor 306 is responsive to the specific anchorage point the lanyard hook 310 is intended to engage. For example, the harness lanyard hook 306-A is intended to engage a D-ring 310 on the harness. The lanyard sensor 306-A in such a case is of the type that is appropriate for the D-ring 210, for example, the sensor 306-A forms part of an electrical circuit with the D-ring 210 when the lanyard hook 306-A is engaged. See FIG. 12. The tower, or anchor, lanyard hook 310-B is of the type suitable for engaging the anchorage point 112 on the tower 110 and the sensor 306-B, 306-C is suitable for the type of anchorage. Because the lanyard connector 308 enables different lanyards 116 to be attached to the harness connector 208, the type of lanyard hooks 310 and sensors 306 on the lanyard 116 are readily configured to be suitable for the climbing environment.

In another embodiment, the hook sensor 306 is connected to a transmitter that communicates with the harness 108. For example, Bluetooth technology allows short-range communications between multiple sensors 306 to a central processor in the harness module 202. Other technologies provide similar short-range communications capabilities.

Figure 4:
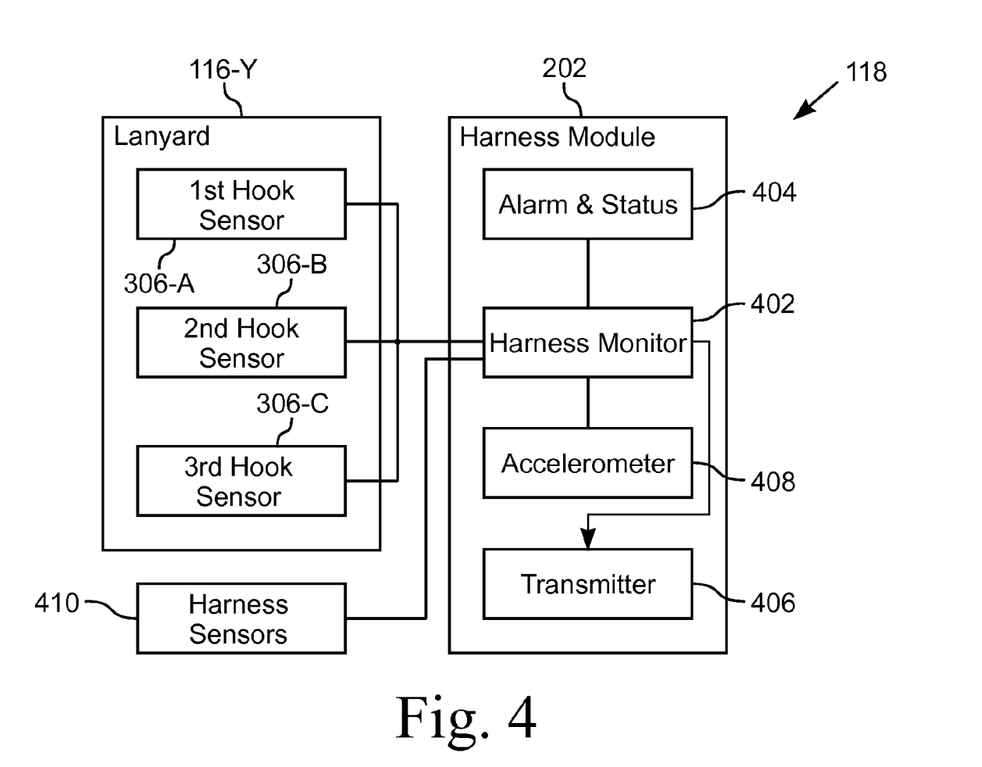
FIG. 4 is a block diagram of one embodiment of a harness system.

FIG. 4 illustrates a block diagram of one embodiment of a harness system 118, which includes at least one lanyard 116-Y and a harness module 202. The illustrated lanyard 116-Y is a connection device with three lanyard hooks 310 that are connected with a flexible member. Each lanyard hook 310 has a hook sensor 306-A, 306-B, 306-C that senses if the corresponding lanyard hook 310 is engaging an anchorage point 112.

The harness module 202 is a portable device worn by the climber 102. The module 202 includes a harness monitor 402, an alarm and status unit 404, an accelerometer 408, and a transmitter 406. The hook sensors 306 communicate with the harness monitor 402, which is a device that includes a circuit that monitors the status of the various sensors 306 and determines if the harness 108 is physically attached to the tower 110 with a connection device (lanyard) 116. The harness sensors 410 are devices that detect the proper connection of the various buckles and fasteners 212 required to be connected for the harness 108 to be securely worn by the climber 102. The harness sensors 410 communicate with the harness monitor 402. In various embodiments, the harness monitor 402 is a controller or processor that receives inputs, such as from the sensors 306, 408, 410, and provides outputs, such as to the alarm and status unit 404 and the transmitter 406.

The accelerometer 408 is a device that senses if the harness monitor 402, and the climber 102 wearing it, has fallen. In one embodiment, the accelerometer 408 measures acceleration and provides an output signal after a threshold acceleration value has been reached. For example, STMicroelectronics Part Number LY530ALH is a gyroscope transducer that provides an analog output. Other devices provide switch contacts. The harness monitor 402 detects the signal from the accelerometer 408 that corresponds to a falling condition of the climber 102. The harness monitor 402, in one embodiment, immediately transmits a signal to the remote monitoring module 114 to alert another person 104 that the climber 102 has fallen.

The alarm and status unit 404 provides information to the climber 102. In various embodiments, the information is provided audibly and visually. The module 202 includes a speaker and a headphone output, which is useful in high noise environments where the speaker would not be audible. In other embodiments, the module 202 includes a siren and/or a vibrator to annunciate alarm conditions, such as when the harness 108 is not physically connected to an anchorage 112 or if the connectors 208, 308 are disconnected. The alarm and status unit 404 also provides indication that the module 202 is powered up and operable.

The transmitter 406 is a device that enables communication with the remote monitoring module 114. The transmitter 406 sends a signal 106 that includes an identification code and information on the status of the harness monitoring system 118. The identification code uniquely identifies the harness system 118 relative to other systems 118 in use within range of the remote monitoring module 114. In one embodiment, the transmitter 406 sends the signal 106 periodically, which enables the remote monitoring module 114 to determine that the harness system 118 is operable. In another embodiment, the transmitter 406 sends the signal 106 when an alarm condition exist, such as when the harness 108 is not physically connected to an anchorage 112, or if the connectors 208, 308 are disconnected, or if a buckle 212 on the harness 108 is not properly connected, or if the accelerometer 408 senses that the climber 102 has fallen.

Figure 5:
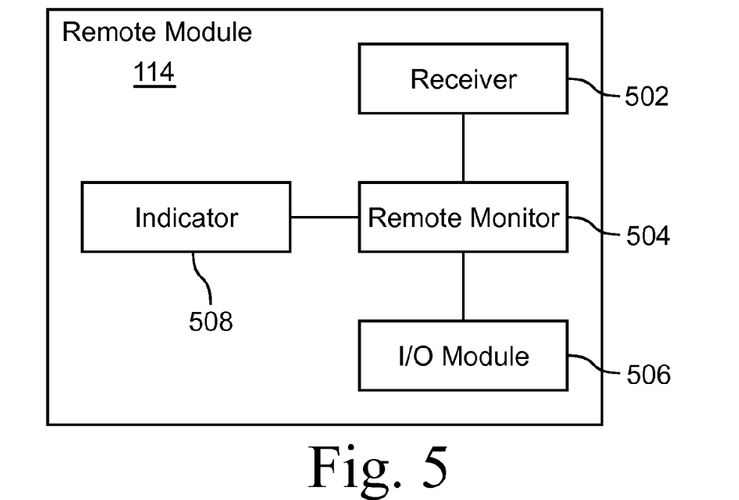
FIG. 5 is a plan view of one embodiment of a Y-lanyard.

FIG. 5 illustrates a block diagram of one embodiment of a remote monitoring module 114. The remote monitoring module 114 is a portable device and includes a receiver 502, a remote monitor 504, an indicator 508, and an input/output (I/O) module 506. The receiver 502 is responsive to the transmitter 406 in the harness module 202. When there are multiple harness systems 118 in use, the receiver 502 is responsive to all the transmitters 406 that are actively sending signals.

The remote monitor 504 is a device that includes a circuit that determines the status of each harness system 118 and provides indication of that status, including any alarms, to the indicator circuit 508 and provides for communicating with other devices and with the operator 104 through the I/O module 506. In various embodiments, the remote monitor 504 is a controller or processor that receives inputs, such as from the receiver 502, and provides outputs, such as to the indicator 508, and an input/output (I/O) module 506.

The indicator module 508 displays to the operator 104 information regarding the status of the remote monitoring module 114 and each harness system 118 being monitored. In one embodiment, the indicator module 508 includes lamps that provide visual indication of the status of each monitored harness system 118 and includes a speaker, siren, and/or headphone output that provides audible indication of an alarm condition, such as when the harness 108 for a climber 108 is not physically connected to an anchorage 112 or if the connectors 208, 308 are disconnected. In another embodiment, the indicator module 508 includes an alphanumeric display that provides status and alarm information.

The I/O module 506 allows the remote monitoring module 114 to communicate with other devices and persons 104. The remote module 114 maintains a log file of the status of the various harness system 118 monitored for a period. That log file is transferred through the I/O module 506 to another device. For example, in one embodiment, the I/O module 506 includes a computer interface that allows a computer to communicate with the remote monitoring module 114 for setting the various parameters of the module 114 and for obtaining the log file. In another embodiment, the harness module 202 stores the log file for later retrieval.

As used herein, the harness monitor 402 and the remote monitor 504 should be broadly construed to mean any device that accepts inputs and provides outputs based on the inputs, for example an analog control device, a controller, or a computer or component thereof that implements the functions of the invention. In various embodiments, the monitors 402, 504 are one of a specialized device or computer for implementing the functions of the invention. The monitors 402, 504 include input/output (I/O) units for communicating with external devices and a processing unit that varies the output based on one or more input values. Computer-based monitors 402, 504 include a memory medium that stores software and data and a processing unit that executes the instructions included in the software and routines.

Figure 6:
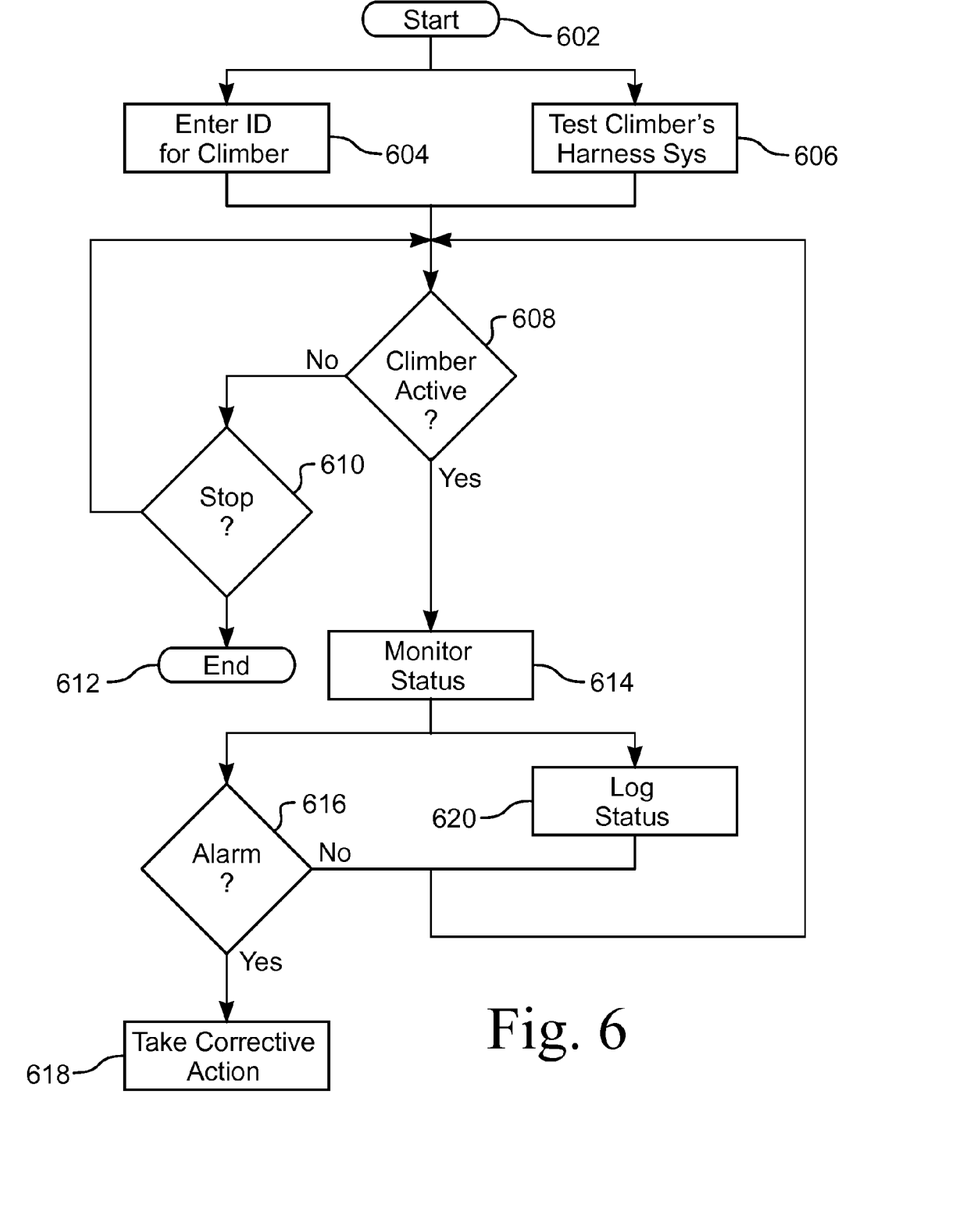
FIG. 6 is a flow diagram of one embodiment of the operation of the personal fall protection monitoring system.

FIG. 6 illustrates a flow diagram of one embodiment of the operation of the personal fall protection monitoring system 100. The first step 602 is to start, which is done when the climbers 102 are ready to don their harnesses 108 to begin climbing. The next step 604 is to enter the identification and/or name of the climber 102 and the harness system 118 to be worn by that climber 102 into the remote monitoring module 114. This step 604 associates the harness system 118 to an input to the remote monitoring module 114.

In conjunction with the step 604 is the step 606 of testing the climber's harness system 118 to verify it is operable and that the remote monitoring module 114 indicates the correct status of the harness system 118. During this step 606, the lanyards 116 to be used by the climber 102 are connected to the harness 108 and the personal fall protection monitoring system 100 is verified to correctly identify the status for all the possible configurations of the system 100. For example, if a single Y-lanyard 116-Y is being used by the climber 102, each lanyard hook 310-B is verified to extinguish an alarm condition when the lanyard hook 310-B engages an anchorage point 112. Also, the sensors 410 for the harness buckles 212 are also tested to ensure they are operable.

After the steps 604, 606 of entering the ID and testing, the next step 608 is to inform the system 100 that the climber 102 is active and needs to be monitored. Until the climber 102 begins ascending the tower 110, it is not necessary to monitor the climber's compliance with the 100% tied off rule. In one embodiment, the harness monitor 402 begins monitoring when the climber 102 first connects to an anchorage point 112 on the tower 110. In another embodiment, the harness monitor 402 begins monitoring when the climber 102 or the operator 104 manually tells the system 100 that the climber 102 is actively ascending.

If the step 608 indicates that the climber 102 is not actively climbing, then the step 610 of deciding to stop is performed. If the operator 104 decides to stop, then the step 612 of ending is performed for that climber. If other climbers are active or entered into the system, the process continues for those climbers 102.

If the step 608 indicates that the climber 102 is actively climbing, then the step 614 of monitoring is performed. Monitoring includes the harness monitor 402 polling the sensors 306, 410 to determine if the climber 102 is in compliance or if there is an equipment failure. The step 614 of monitoring also includes the remote monitoring module 114 monitoring the status of the climber's harness system 118.

The step 616 of checking for an alarm condition is performed after each status check of step 614. If there is an alarm condition, the step 618 of taking corrective action is initiated. Corrective action includes an action such as communicating with the climber 102 to have the climber 102 ensure that he is in a safe condition. Action also includes an action such as having the climber 102 verify the integrity of the connections 208, 212, 308.

The step 620 of logging the status is performed after the status check of step 614. The remote monitoring module 114 records the status of each climber 102 and makes the log available for later use. In one embodiment, the log data includes data from each status check of step 614. In another embodiment, the log data includes only data regarding when the climber 102 became active, when an alarm condition occurs, and when the climber 102 leaves active status.

If there is no alarm condition and after the status is logged, the next step 608 is to check to ensure the climber 102 is active. By looping in this way, monitoring continues for the period that the climber 102 is aloft and is terminated when the climber 102 is no longer actively climbing and the climber 102 is not required to use the personal fall protection monitoring system 100.

Figure 7:
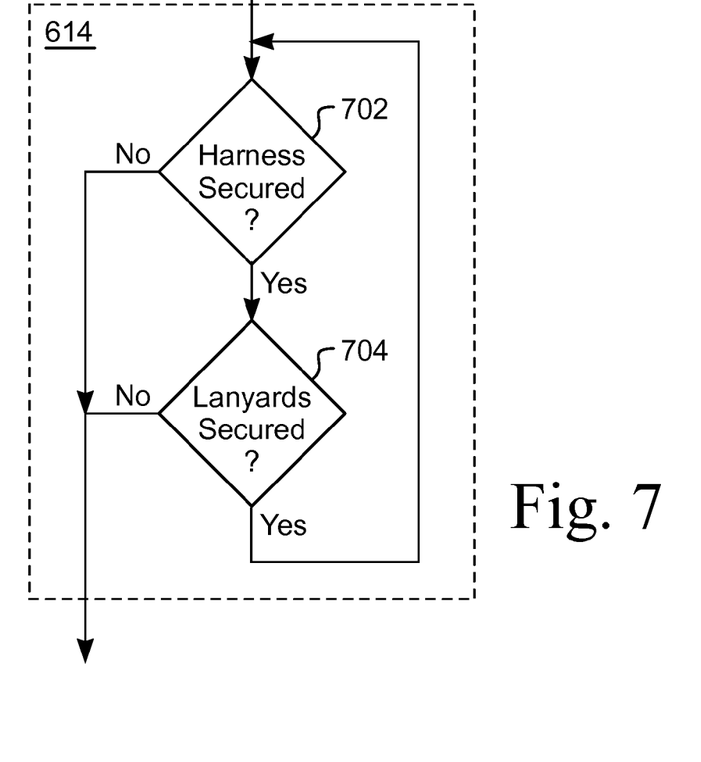
FIG. 7 is a flow diagram of a status monitor.

FIG. 7 illustrates a flow diagram of the step 614 of monitoring status. The step 614 of monitoring includes a step 702 of checking if the harness 108 is secured. For the embodiment in which the harness module 202 monitors the various buckles and fasteners 212 of the harness 108, the buckles 212 are checked to ensure that they are properly connected. If the buckles 212 are not properly fastened, the step 614 exits for alarm condition checking 616 and for data logging 620. Many harnesses 108 require the wearer 102 to fasten several components to secure the harness 108 to the body. A danger exists to the climber 102 if any of the buckles or fasteners 212 are not properly connected. If, for example, a climber 102 fails to attach the straps that secure the legs, in the event of a fall, the harness 102 would simply slide off the body of the climber 102 providing no protection against the fall. In such a case, the harness 108 provides the climber 102 a false sense of security because in reality, if it is not completely fastened, it offers little or no protection.

If the buckles 212 are properly connected, the next step 704 is to check that the lanyards 116 are properly attached to an anchor 112. If the lanyards 116 are not properly fastened, the step 614 exits for alarm condition checking 616 and for data logging 620. If the lanyards 116 are properly fastened, the step 614 repeats until either a harness buckle 212 or a lanyard 116 is not properly connected. Those skilled in the art will recognize that the steps 702, 704 of checking the harness buckles 212 and lanyards 116 can be performed in either order or simultaneously without departing from the spirit and scope of the present invention.

In one embodiment, the step 704 of checking that the lanyards 116 are properly attached includes verifying that the outboard lanyard hook 306-B, 306-C is not attached to a D-ring 210 on the harness 108. Often, when a climber 102 is not climbing, the climber 102 attaches the loose ends of the halyards 116 to the harness 108 so that the outboard ends of the halyards 116 do not drag on the ground. The various embodiments of the halyard hooks 310 configured to detect an anchor 112 will likewise detect the D-ring 210. In this embodiment, the halyard hooks 310-F, 310-G detect the presence of the D-ring 210, 210' and the step 704 of checking will return no, the lanyard 116 is not properly attached to an anchor 112.

Figure 8:
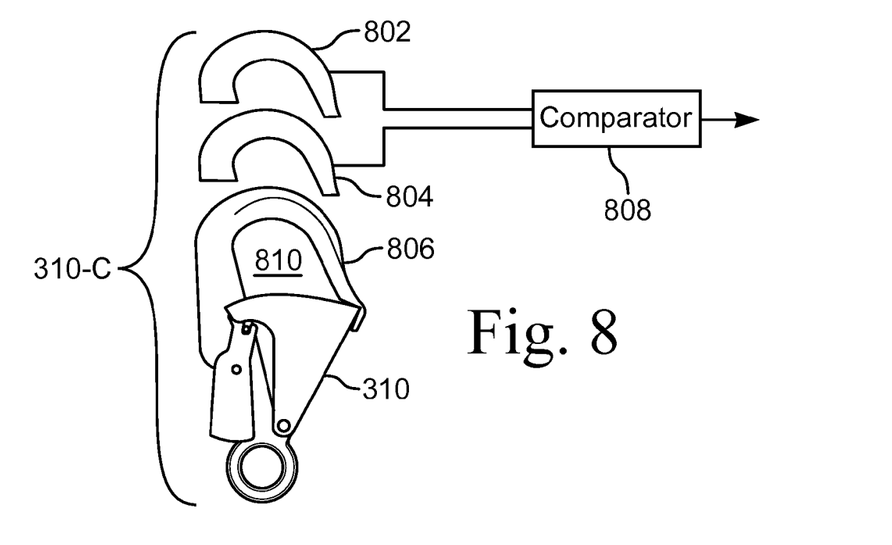
FIG. 8 is a diagram showing one embodiment of a lanyard hook using radio frequency connection detection.

FIG. 8 illustrates a diagram showing one embodiment of a lanyard hook 310-C using radio frequency connection detection. In the illustrated embodiment, the lanyard hook 310-C is part of a radio frequency (RF) detection system where an RF signal is injected into the structure 110. For example, the RF signal can be provided by a device such as the Extech TG30 Wire Tracer/Tone Generator Kit, which loads a wire with a signal, or the Amprobe AT-3000 PRO Underground Hawk Buried Wire & Pipes Locator. These devices inject an RF signal into a conductive material, such as the structure 110, if it is a metal tower.

In order for the lanyard hook 310-C to determine if the hook 310-C is properly attached, the hook 310-C includes two metal sensors 802, 804 attached to a hook 310. The metal sensors 802, 804 are the same size and shape. The first metal sensor 802 is an attachment detector that is exposed such that it touches the structure 110 when the lanyard hook 310-C is properly attached. The second metal sensor 804 is an ambient detector that is electrically insulated from the structure 110. The first and second sensors 802, 804 are each electrically connected to an input of a comparator 808. Those skilled in the art will recognize that such an electrical connection can be made through a capacitive network such that a signal corresponding to the RF signal is passed to the comparator 808. The comparator 808 compares the signal from the attachment detector 802 and the ambient detector 804. When the lanyard hook 310-C is proximate the structure 110, but not contacting it, the signals from the attachment detector 802 and the ambient detector 804 are equal and the comparator 808 determines that there is no difference between the signals. When the lanyard hook 310-C is attached to the structure 110 the attachment detector 802 contacts the structure 110 and has a higher signal strength than the ambient detector 804, which picks up the RF signal through radiation, not conduction. When the lanyard hook 310-C is attached, the comparator 808 determines that there is a differential between the signals from the attachment detector 802 and the ambient detector 804. The comparator 808 in such a case has an output indicating that the lanyard hook 310-C is attached to the structure 110. In one embodiment the differential between the attachment detector 802 and the ambient detector 804 that indicates attachment of the lanyard hook 310-C is adjustable to accommodate the characteristics of the structure 110 to be climbed.

In one embodiment, the ambient detector 804 is an insulated foil or thin metal that conforms to the shape of part of the hook portion 806 of the lanyard hook 310-C. The hook portion 806 is the bend of the hook 310 and extends from the shank connecting the hook portion 806 to the eye 906 to the gate that is closed by the safety latch 902. The attachment detector 802 is a foil or thin metal that likewise conforms to the shape of part of the hook portion 806 of the lanyard hook 310-C. The attachment detector 802 is attached such that the exposed metal of the detector 802 contacts the structure 110 when the lanyard hook 310-C is properly attached to the structure 110. One such configuration is with the attachment detector 802 lining the inside opening 810 of the lanyard hook 310-C.

Figure 9:
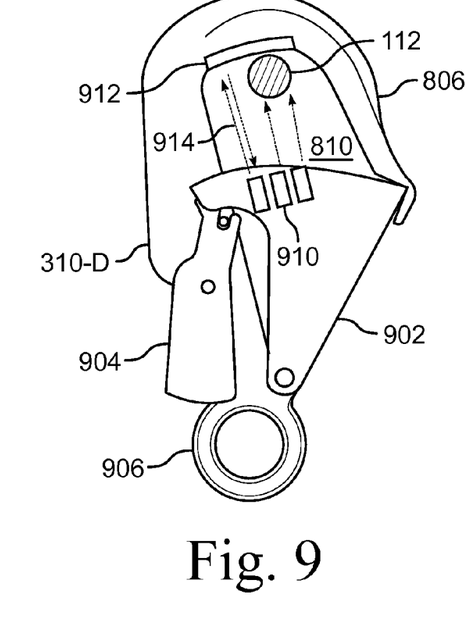
FIG. 9 is a diagram showing one embodiment of a lanyard hook with an optical connection detector.

FIG. 9 illustrates a diagram showing one embodiment of a lanyard hook 310-D with an optical connection detector. The lanyard hook 310-D includes a hook portion 806 that engages a safety latch 902. The safety latch 902 is locked in place with a lock 904. Opposite the hook portion 806 is an eye 906 configured to attach to the lanyard strap 312. Between the hook portion 806 and the safety latch 902 is an opening 810 dimensioned and configured to receive an anchor 112. Typically, the weight of the lanyard hook 310 and the lanyard strap 312 is sufficient to maintain the lanyard hook 310 in the illustrated position with the hook portion 806 at the top.

The lanyard hook 310-D includes reflective photo sensors 910 that each emit a beam 914 that is reflected from a reflector 912 back to the reflective photo sensor 910. For example, Sharp Microelectronics model number GP2Y0D810Z0F emits a beam of infrared radiation and is responsive to its reflection. If the emitted beam is interrupted before being received by the device, the device indicates the presence of a blocking material, such as an anchor 112.

In the illustrated embodiment, three reflective photo sensors 910 are arranged on the safety latch 902 so as to ensure substantial coverage of the opening 810. That is, the beams 914 are spaced sufficiently close together and cross the opening 810 such that the anchor 112 must break at least one beam 914 when engaged by the lanyard hook 310-D. By ensuring that the gap between the beams 914 and the gap between the outer beams 914 and the inside surface of the opening 810 is dimensioned less than the smallest dimension of the expected anchor 112, at least one photo sensor 910 will detect the presence of the anchor 112 in the opening 810. The reflector 912 is positioned on the opposite side of the opening 810 to reflect the emitted beams 914 back to the respective reflective photo sensors 910. For the embodiment where cross-talk or interference between adjacent reflective photo sensors 910 is to be minimized, modulation, polarization, and/or sequencing the individual sensors 910 are employed.

The reflective photo sensors 910 and the reflector 912, in one embodiment, are recessed in the lanyard hook 310-D and may be covered with a transparent material for protection. In another embodiment, the reflective photo sensors 910 and reflector 912 are in a housing attached to the lanyard hook 310-D.

Those skilled in the art will recognize that the number of reflective photo sensors 910 will vary depending upon the size of the opening 810 and the minimum expected size of the anchor 112. In one embodiment, a single reflective photo sensor 910 is used. The single sensor 910 is aimed at the sweet spot of the hook 310-D, which is the spot in the opening 810 where the anchor 112 is most likely to be positioned during use. In various embodiments, an integrator or time sampling technique is used to prevent false alarms when the anchor 112 temporarily moves out of the sweet spot while the lanyard hook 310-D is still engaging the anchor 112. In other embodiments, the reflective photo sensor 910 emits a wide beam 914 or a scanning beam that sweeps through the opening 810.

Figure 10:
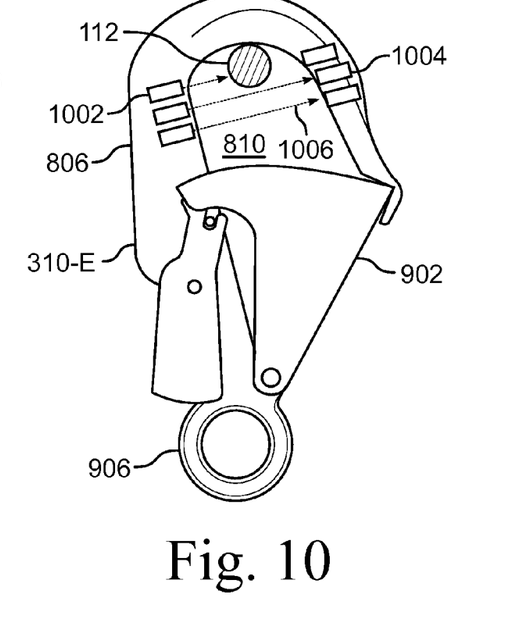
FIG. 10 is a diagram showing another embodiment of a lanyard hook with an optical connection detector.

FIG. 10 illustrates a diagram showing another embodiment of a lanyard hook 310-E with an optical connection detector. In the illustrated embodiment, a group of emitters 1002 transmits beams 1006 to receivers 1004 in a through-beam photo sensor configuration. An object, such as an anchor 112, that interrupts one of the beams 1006 indicates that the lanyard hook 310-E is attached to the anchor 112.

The lanyard hook 310-E includes emitters 1002 that each emit a beam 1006 that is received by a corresponding receiver 1004. For example, the emitters 1002 are Sharp Microelectronics model number PT100MF0MP1, which emit infrared radiation at 900 nm and the receivers 1004 are Sharp Microelectronics model number GL100MN0MP1, which filters radiation outside the 900 nm band. If the emitted beam is interrupted before being received by the device, the device indicates the presence of a blocking material, such as an anchor 112.

In the illustrated embodiment, three emitters 1002 are arranged on one side of the hook portion 806 so as to ensure substantial coverage of the opening 810. That is, the beams 1006 are spaced sufficiently close together and cross the opening 810 such that the anchor 112 must break at least one beam 1006 when engaged by the lanyard hook 310-E. By ensuring that the gap between the beams 1006 and the gap between the outer beams 1006 and the inside surface of the opening 810 is dimensioned less than the smallest dimension of the expected anchor 112, at least one receiver 1004 will detect the presence of the anchor 112 in the opening 810. The receivers 1004 are positioned on the opposite side of the opening 810 to receive the emitted beams 1006 from the respective emitters 1002. For the embodiment where cross-talk or interference between adjacent reflective photo sensors 910 is to be minimized, modulation, polarization, a collimator 1102, and/or sequencing the individual emitters 1002 are employed. For example, the emitters 1002 are energized sequentially and the corresponding receiver 1004 is monitored for a beam 1006. In such a case, the receivers 1004 are multiplexed to a single filtering and detection circuit.

The emitters 1002 and the receivers 1004, in one embodiment, are recessed in the hook portion 806 and may be covered with a transparent material for protection. In another embodiment, the emitters 1002 and the receivers 1004 are in a housing attached to the hook 310-E.

Those skilled in the art will recognize that the number of emitters 1002 and receivers 1004 will vary depending upon the size of the opening 810 and the minimum expected size of the anchor 112. In one embodiment, a single emitter 1002 and receiver 1004 are used. The emitter 1002 and receiver 1004 are aimed at the sweet spot of the hook 310-E, which is the spot in the opening 810 where the anchor 112 is most likely to be positioned during use. The sweet spot is typically the top of the opening 810. In various embodiments, an integrator or time sampling technique is used to prevent false alarms when the anchor 112 temporarily moves out of the sweet spot while the lanyard hook 310-E is still engaging the anchor 112. In other embodiments, the single emitter 1002 emits a wide beam 1006 or a scanning beam that sweeps through the opening 810 and impinges upon the receiver 1004.

In one embodiment of the lanyard hook 310-E, the emitters 1002 and receivers 1004 are separated such that the distance separating the beams 1006 is less than the smallest dimension of the anchor 112. For example, the beams 1006 separated by a distance of ⅛ inch. An anchor 112 that is ⅜ inch in diameter will interrupt at least two beams 1006 and at most three beams 1006. Knowing the number of beams 1006 that are interrupted, the size of the anchor 112 is calculated with an uncertainty of plus or minus the distance between adjacent beams 1006. In this example, if two beams 1006 are interrupted, the anchor 112 must be no larger than ⅜ inch and no less than ⅛ inch in diameter. To reduce the uncertainty, the distance between beams 1006 is reduced. In one embodiment of the lanyard hook 310-D, the reflective photo sensors 910 are separated in a similar manner.

In one such embodiment, the harness monitor 402 is programmed to detect a proper attachment of a lanyard hook 310 when the detected anchor 112 is determined to be a specified size. For example, if a particular task requires that a minimum ¾ inch anchor 112 be used, the harness monitor 402 will not indicate a proper attachment unless the detected anchor 112 interrupts the required number of beams 914, 1006. In one such embodiment, the D-Ring 210 is smaller than the minimum anchor 112 and the harness monitor 402 is able to differentiate between an anchor 112 and a D-Ring 210. In this case, the harness monitor 402 is able to determine if the lanyard hook 310 is properly attached to an anchor 112 and not a D-ring 210, such as when the climber 102 is storing the outboard hook 310-B of the lanyard 116 on the harness 108.

In another embodiment of the lanyard hook 310-E, the multiple emitters 1002 and receivers 1004 are energized for a brief time sufficient for the devices to determine if the corresponding beam 1106 is interrupted. In this way the power consumption is minimized because the devices are only energized sufficiently long to detect their current state. Also, by sequencing the energization of the devices, the maximum power at any one time is minimized. In another embodiment of the lanyard hook 310-D, the multiple reflective photo sensors 910 are separated in a similar manner.

Figure 11:
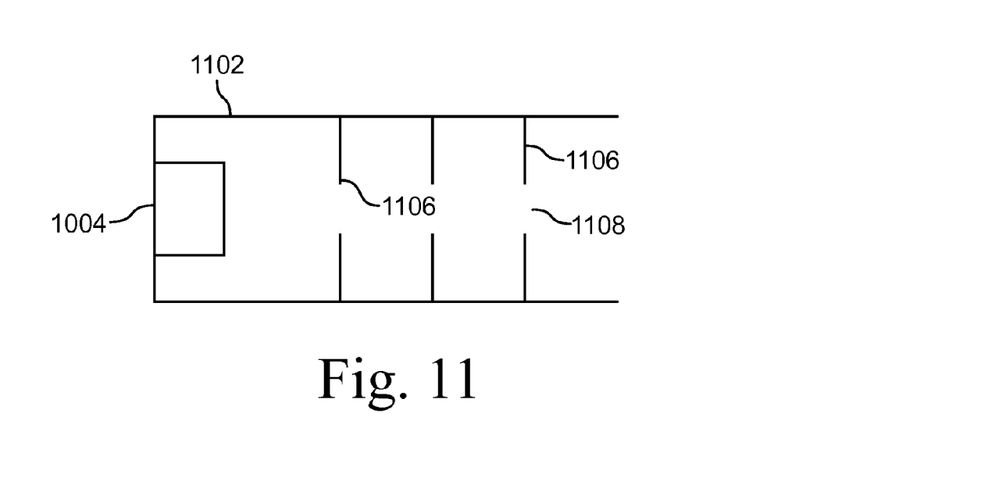
FIG. 11 is a schematic diagram of one embodiment of a collimator and optical receiver.

FIG. 11 illustrates a schematic diagram of one embodiment of a collimator 1102 and receiver 1104. In various embodiments, the receiver 1104 is recessed or protected from stray radiation, which could cause a false connection to be indicated between the emitter 1002 and the corresponding receiver 1004. In one such embodiment, the receiver 1004 is coupled with a collimator 1102. The collimator 1102 is a tubular structure with at least one baffle 1106. A baffle 1106 is a plate with a central opening 1108. Light entering the tube of the collimator 1102 is blocked except for light that travels along the axis of the collimator 1102. The axis of the collimator 1102 is coaxial with the central openings 1108. In this way, stray light is reduced and the receiver 1004 is responsive only to the beam 1006 emitted by the corresponding emitter 1002 that is aligned with the axis of the collimator 1102.

In one such embodiment, the internal surfaces of the collimator 1102 are coated with a black, non-reflective material. In this way, reflected stray light is reduced.

Figure 12:
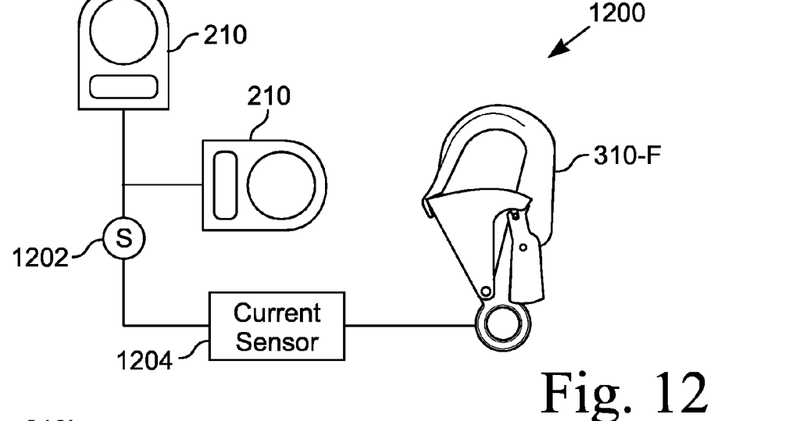
FIG. 12 is a schematic diagram of one embodiment of a lanyard to harness detection system.

FIG. 12 illustrates a schematic diagram of one embodiment of a lanyard to harness detection system 1200. The detection system 1200 includes an electrical source 1202 that is electrically connected between all the available D-rings 210 on the harness 108 and a current sensor 1204. The current sensor 1204 is connected between the electrical source 1202 and the lanyard hook 310-F. When the lanyard hook 310-F is attached to a D-ring 210, the electrical circuit is completed and the current detector 1204 detects a loop current and indicates to the harness monitor 402 that the halyard hook 310-F is connected to the harness 108. For the case where the halyard hook 310-F is the inboard hook 310-A, the harness monitor 402 determines that the halyard hook 310-A, 310-F is properly attached. Where the halyard hook 310-F is the outboard hook 310-B, the harness monitor 402 determines that the halyard hook 310-BA, 310-F is not properly attached.

In another embodiment, the webbing of the harness 108 is conductive. In this way, if the lanyard hook 310-F is hooked to the harness webbing, electrical contact is made and the current sensor 1204 detects that the hook 310-F is attached to the harness. In such an embodiment, the source 1202 provides an alternating current signal that is detectable by the current sensor 1204.

In one embodiment, the electrical source 1202 is the output from a direct current power supply that applies a voltage between the D-rings 210 and the current sensor 1204. In another embodiment, the electrical source 1202 is a signal generator, such as one that produces an alternating current signal, a pulsed signal, or a modulated signal. In such an embodiment, the current sensor 1204 detects the signal and if the detected signal matches the signal from the source 1202, the harness monitor 402 determines that the lanyard hook 310-F is connected to a D-ring 210.

In one embodiment, the current sensor 1204 is a relay that is energized when sufficient current flows through the coil. The contacts of the relay are connected to the harness monitor 402. In another embodiment, the current monitor 1204 is an opto-isolator with the output of the opto-isolator connected to the harness monitor 402.

For the case where the lanyard hook 310-F is the outboard hook 310-B of the lanyard 318, when the current sensor 1204 detects that the hook 310-B, 310-F is attached to the harness 108, the harness monitor 402 determines that the hook 310-B, 310-F is not attached to a safe anchor 112. For the case where the lanyard hook 310-F is the inboard hook 310-A of the lanyard 318, when the current sensor 1204 detects that the hook 310-B, 310-F is attached to a D-ring 210 of the harness 108, the harness monitor 402 determines that the hook 310-B, 310-F is properly attached to the harness 108.

Figure 13:
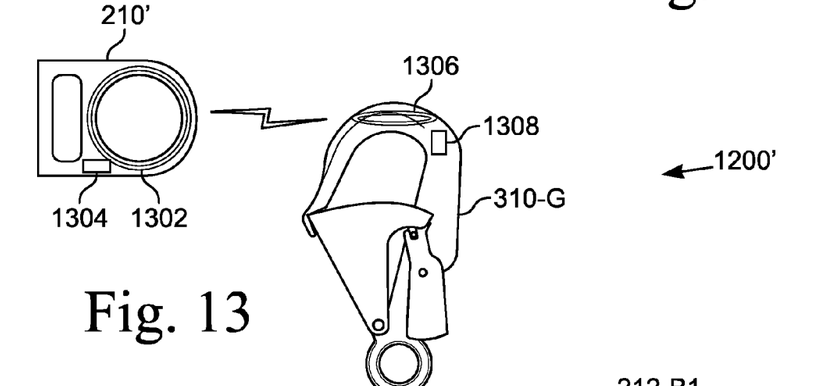
FIG. 13 is a schematic diagram of one embodiment of an RFID lanyard to harness detection system.

FIG. 13 illustrates a schematic diagram of one embodiment of an RFID lanyard to harness detection system 1200'. Radio frequency identification devices (RFID) operate over short distances. In the illustrated embodiment, the D-ring 210' includes an RFID antenna 1302 and an RFID transponder 1304 that provides the signal to the antenna 1302. In another embodiment, the RFID antenna 1302 and an RFID transponder 1304 are attached to the webbing next to the D-ring 210' and at regular intervals on the webbing of the harness 108. In yet another embodiment, the RFID antenna 1302 and an RFID transponder 1304 are positioned in flaps or pockets either integral with the webbing or attached to the webbing. Each RFID antenna 1302 and an RFID transponder 1304 pair have a different transponder code that identifies the specific D-ring 210' or location on the webbing. The lanyard hook 310-G includes an RFID reader antenna 1306 attached to the hook portion 806 and an RFID reader 1308. The RFID system 1200' is configured to operate over a short distance, for example, 100 mm.

In various embodiments, the antenna 1302 on the D-ring 210' is encapsulated with a material such as potting compounds, epoxies, urethanes, and plastics. In one such embodiment, a durable housing is made out of UHMW or similar material that is positioned over the antenna 1302 attached to the side of the D-ring 210'. Similar encapsulation methods are applied to the antenna 1306 on the hook portion 806. In one embodiment, the antennas 1302, 1306 are employed on both sides of the D-ring 210' and the hook portion 806 to make detection more reliable.

When the lanyard hook 310-G is positioned proximate the D-ring 210', such as when they are connected, the RFID reader 1308 senses the RFID transponder 1304 signal. The RFID reader 1308 communicates with the harness monitor 402, which determines that the lanyard hook 310-G is attached to a D-ring 210' or the webbing.

Figure 14:
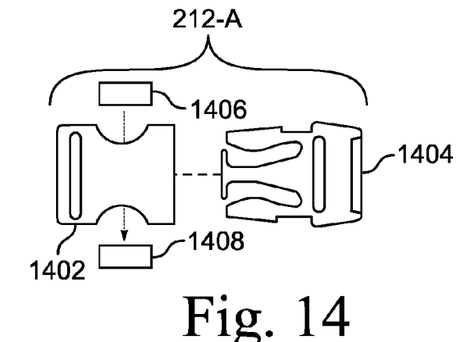
FIG. 14 is a symbolic diagram of one embodiment of a harness buckle with a connection sensor.

FIG. 14 illustrates a symbolic diagram of one embodiment of a harness buckle 212-A with a connection sensor 1406, 1408. The buckle 212-A is a side-squeeze type buckle with a male piece 1404 and a female piece 1402. The female piece 1402 has a cavity that receives the male piece 1404. An optical through-beam sensor system with an emitter 1406 and a receiver 1408 is positioned to pass a beam through the cavity of the female piece 1402. When the male piece 1404 is inserted in the female piece 1402, the receiver 1408 detects the interrupted beam. The receiver 1408 communicates with the harness monitor 402, which determines that the buckle 212-A is fastened.

In one embodiment, the emitter 1406 is attached to one of the female or male pieces 1402, 1404 and the receiver 1408 is attached to the other 1402, 1404. The emitter 1406 sends a coded or modulated signal that is unique to the buckle pieces 1402, 1404. The receiver 1408 is responsive to the signal and if the received signal does not match the expected emitted signal, then the two buckle halves 1402, 1404 are not matched and the harness 108 is not being properly worn.

In yet another embodiment, a reflective photo sensor is positioned on one of the female or male pieces 1402, 1404 and a reflector is attached to the other 1402, 1404. When the male piece 1404 engages the female piece 1402, the reflector is positioned to reflect the beam from the reflective photo sensor back to itself. The reflective photo sensor communicates with the harness monitor 402, which determines that the buckle 212-A is connected. In one such embodiment, the reflector has the characteristic of uniquely polarizing or filtering the reflected beam for a specific buckle 212-A. The reflective photo sensor is responsive the reflector and if unmatched pieces 1402, 1404 are connected, the harness monitor 402 detects the mismatch.

In still another embodiment, an RFID transponder and an RFID reader are attached on or adjacent the buckle 212-A, such as illustrated with the hook 310-G and D-ring 210' in FIG. 13. With the buckle 212-A fastened, the RFID transponder and the RFID reader are brought together, thereby communicating to the harness monitor 402 that the buckle 212-A is fastened. For the embodiment in which the transponder has a unique code matched to the reader, if unmatched pieces 1402, 1404 are connected, the harness monitor 402 detects the mismatch.

Figure 15:
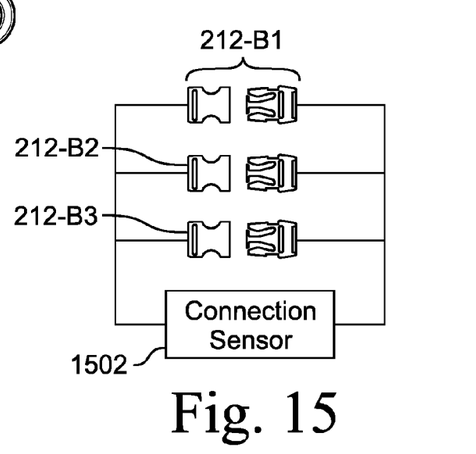
FIG. 15 is a schematic diagram of another embodiment of a harness buckle with a connection sensor.

FIG. 15 illustrates a schematic diagram of another embodiment of a harness buckle 212-B with a connection sensor 1502. In the illustrated embodiment, the buckles 212-B1, 212-B2, 212-B3 or a portion thereof are conductive. Each buckle 212-B1, 212-B2, 212-B3 is wired in parallel and connected to a connection sensor 1502, which determines when a buckle 212-B1, 212-B2, 212-B3 is fastened.

In one embodiment, each buckle 212-B1, 212-B2, 212-B3 is wired to the connection sensor 1502 individually. In this way the connection sensor 1502 can determine if there is a mismatch between halves of the buckles 212-B1, 212-B2, 212-B3. In one such embodiment, the wired buckles 212-B1, 212-B2, 212-B3 each have a unique coded signal. The connection sensor 1502 determines if the coded signal sent on one wire is received over the corresponding wire connected to the corresponding half of the buckle 212-B1, 212-B2, 212-B3. In this way the connection sensor 1502 can determine if there is a mismatch between halves of the buckles 212-B1, 212-B2, 212-B3.

The personal fall protection monitoring system 100 includes various functions. The function of informing a climber 102 of non-compliance with the 100% tied off rule is implemented, in one embodiment, by the harness system 118, which includes the alarm and status module 404 that annunciates an alarm condition to the climber 102.

The function of informing another person 102 of non-compliance with the 100% tied off rule is implemented, in one embodiment, by the harness system 118 communicating compliance status information with the remote monitoring module 114, which includes an indicator module 508 that provides real-time status and alarm information to a person 104.

The function of maintaining log data is implemented, in one embodiment, by the remote monitoring module 114, which includes a remote monitor 504 that records status data in a log file. In another embodiment the function of maintaining log data is implemented by the harness monitor 202 including a storage component that records status data in a log file.

From the foregoing description, it will be recognized by those skilled in the art that a personal fall protection monitoring system 100 has been provided. The system 100 is suitable for field use and aids in ensuring compliance with the 100% tied off rule. The system 100 is readily configured to be retrofitted to existing harnesses 108, as well as being provided as an integrated system. The harness module 202 and the remote monitoring module 114 are portable, battery operated devices suitable for use in the field.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for a personal fall protection monitoring system, said apparatus comprising:
 a harness monitoring system that includes
  a lanyard with a first hook and a second hook, said first hook having a first sensor, said first sensor detecting a secured condition when said first hook has engaged an anchor, said first sensor detecting an unsecured condition when said first hook is disengaged from said anchor,
  a harness configured to be worn by a first person, said second hook securable to said harness,
  a first monitor in communication with said first sensor, said monitor responsive to a signal from said first sensor, and
  a transmitter in communication with said first monitor, said transmitter sending a first signal when said sensor detects said unsecured condition of said first hook;
 a second sensor detecting a lanyard stored condition when said first hook is attached to said harness, said second sensor communicating with said first monitor, and said transmitter sending said first signal when said sensor detects said lanyard stored condition; and
 a remote module physically unattached to said harness monitoring system, said remote module including
  a receiver responsive to said transmitter, and
  a second monitor in communication with said receiver, said second monitor responsive to said unsecured condition of said first hook.

2. The apparatus of claim 1 wherein said second monitor includes an output that provides indication to a second person of said unsecured condition.

3. The apparatus of claim 1 wherein said harness monitoring system further includes a second sensor responsive to a falling condition; said transmitter sending a second signal when said second sensor detects said falling condition; and said second monitor having an output of an alarm in response to said falling condition.

4. The apparatus of claim 1 further including a third sensor detecting when said second hook is not attached to said harness; said third sensor communicating with said first monitor; and said first monitor having a second output signal indicating when said second hook is not attached to said harness.

5. The apparatus of claim 1 wherein said first sensor detects said unsecured condition when said first hook is engaging said harness.

6. The apparatus of claim 1 wherein said harness includes a buckle having a pair of buckle halves, said pair of buckle halves configured to secure said harness to said first person when said pair of buckle halves are mated; and said harness further including a buckle sensor, said buckle sensor detecting an unbuckled condition when a pair of buckle halves are separated; and said monitor having a second output signal indicating said unbuckled condition.

7. The apparatus of claim 1 wherein said first sensor includes a sensor receiver responsive to a beam from a sensor emitter; said beam traversing an opening of said first hook configured to receive said anchor; and said first sensor detecting said unsecured condition when said beam is uninterrupted.

8. The apparatus of claim 1 wherein said first sensor includes a sensor receiver responsive to a beam from a sensor emitter; said beam traversing an opening of said first hook configured to receive said anchor; said sensor receiver positioned on a first side of said opening, said sensor receiver positioned on a side of said opening opposite said first side; and said first sensor detecting said unsecured condition when said beam is uninterrupted.

9. An apparatus for a personal fall protection monitoring system working in conjunction with a harness configured to be worn by a person and to support the person when a fall is prevented, said apparatus comprising:
 a first hook having a hook portion and a safety latch, said first hook configured to receive an anchor through a gate defined by the interface of said hook portion and said safety latch;
 a first sensor responsive to said anchor when said anchor is captive in said first hook;
 a second sensor detecting when said first hook is attached to an attachment point on the harness;
 a first lanyard having a first end attached to said first hook, said first lanyard having a second end configured to attach to the harness; and
 a monitor in communication with said first sensor and said second sensor, said monitor configured to attach to the harness, said monitor having a first output signal corresponding to when said anchor is not captive in said first hook, said monitor having a second output signal corresponding to when said first hook is engaged with said attachment point on the harness, and wherein said monitor differentiates between said first hook being attached to said anchor and to said attachment point on the harness.

10. The apparatus of claim 9 further including a transmitter in communication with said monitor, said transmitter sending a signal to a remote receiver; and said signal indicating a status of said first sensor.

11. The apparatus of claim 9 further including a second sensor responsive to a falling condition; said monitor communicating with a transmitter that sends a first signal when said second sensor detects said falling condition.

12. The apparatus of claim 9 further including a buckle and a buckle sensor, said buckle having a pair of buckle halves, said pair of buckle halves configured to secure the harness to the person when said pair of buckle halves are mated; said buckle sensor detecting an unbuckled condition when a pair of buckle halves are separated; and said monitor having a second output signal indicating said unbuckled condition.

13. The apparatus of claim 9 further including a second hook attached to an end of said lanyard opposite said first hook; said second hook configured to mate with said harness; a third sensor detecting when said second hook is attached to said harness; said third sensor communicating with said monitor; and said monitor having a second output signal indicating when said second hook is not attached to said harness.

14. The apparatus of claim 9 wherein said first sensor includes a sensor receiver responsive to a beam from a sensor emitter; said beam traversing an opening of said first hook configured to receive said anchor; and said first sensor detecting said unsecured condition when said beam is uninterrupted.

15. The apparatus of claim 9 wherein said first sensor includes a sensor receiver responsive to a beam from a sensor emitter; said beam traversing an opening of said first hook configured to receive said anchor; said sensor receiver positioned on a first side of said opening, said sensor receiver positioned on a side of said opening opposite said first side; and said first sensor detecting said unsecured condition when said beam is uninterrupted.

16. An apparatus for a personal fall protection monitoring system for a harness worn by a person and that supports the person when a fall is prevented, said apparatus comprising:

a monitor having a first input from a first sensor, said first input receiving a first signal corresponding to one of a first hook unsecured condition and a first hook secured condition, said monitor connected to a second sensor that detects a falling condition, said monitor configured to be attached to the harness; a transmitter in communication with said monitor, said transmitter sending a second signal corresponding to said first hook unsecured condition, said transmitter sending a third signal corresponding to a detection of said falling condition; a receiver in wireless communication with said transmitter and receiving said second signal and said third signal; wherein said first hook is attached to a distal end of a lanyard that is attached to the harness, said first hook including said first sensor that is responsive to an external anchor to indicate when said first hook is deployed and engaging an external anchor, and a third sensor detecting when said first hook cooperates with an attachment point on the harness to indicate when said first hook is not deployed on an anchor but is stored on the harness, said third sensor connected to said monitor, said transmitter sending a fourth signal corresponding to a stored condition of said first hook with respect to said attachment point on the harness, wherein said monitor differentiates between said first hook being attached to said external anchor and to said attachment point on the harness.

17. The apparatus of claim 16 wherein said first hook unsecured condition is defined as a first hook being unsecured to an external anchor, wherein said first hook is attached to a lanyard that is attached to the harness.

18. The apparatus of claim 16 further including an output from said receiver, said output connected to a remote monitor, and said remote monitor storing a status of the monitor in a log file for later retrieval.

* * * * *